United States Patent [19]

Gordon

[11] Patent Number: 4,610,241
[45] Date of Patent: Sep. 9, 1986

[54] ATHEROSCLEROSIS TREATMENT METHOD

[76] Inventor: Robert T. Gordon, 4936 W. Estes, Skokie, Ill. 60077

[21] Appl. No.: 627,423

[22] Filed: Jul. 3, 1984

[51] Int. Cl.⁴ .............................................. A61B 17/52
[52] U.S. Cl. .......................................... 128/1.3; 424/9
[58] Field of Search .................. 128/1 R, 1.1, 1.3, 1.5, 128/399, 653, 654, 786; 424/9; 252/62, 56

[56] References Cited

U.S. PATENT DOCUMENTS

| | | | |
|---|---|---|---|
| 4,224,313 | 9/1980 | Zimmermann et al. | 128/1.1 |
| 4,269,826 | 5/1981 | Zimmermann et al. | 128/1.1 |
| 4,303,636 | 12/1981 | Gordon | 128/1.1 |
| 4,323,056 | 4/1982 | Borrelli et al. | 128/1.3 |
| 4,335,094 | 6/1982 | Mosbach | 424/9 |
| 4,359,453 | 11/1982 | Gordon | 128/1.1 |
| 4,392,040 | 7/1983 | Rand et al. | 128/1.5 |
| 4,452,773 | 6/1984 | Molday | 424/9 |

Primary Examiner—Edward M. Coven
Assistant Examiner—Max F. Hindenburg
Attorney, Agent, or Firm—Scully, Scott, Murphy and Presser

[57] ABSTRACT

A treatment of atherosclerosis by the application of external electromagnetic energy capable of the generation of heat and biophysical alterations in any electric or magnetic dipole present or capable of being induced within the atherosclerotic plaque and the cells contained therein. This process allows for the selective treatment of the atherosclerotic plaque without damaging the normal blood vessel by the compartmentalized alteration of biophysical and/or structural properties within the atherosclerotic lesion.

16 Claims, No Drawings

ATHEROSCLEROSIS TREATMENT METHOD

FIELD OF THE INVENTION

This invention relates generally to a process and composition for the treatment of atherosclerosis by the application of external electromagnetic energy capable of the generation of heat and biophysical alterations in any electric or magnetic dipole present or capable of being induced within the atherosclerotic plaque and the cells contained therein. This process allows for the selective treatment of the atherosclerotic plaque without damaging the normal blood vessel by the compartmentalized alteration of biophysical and/or structural properties within the atherosclerotic lesion.

BACKGROUND OF THE INVENTION

There are presently a number of methods and techniques for the treatment of atherosclerosis among which may be included chemotherapy and surgery. Chemotherapeutic attempts have centered around decreasing serum lipid (cholesterol and triglyceride) levels or altering the metabolism in order to affect the scattered atherosclerotic lesions throughout the body. Surgery is only effective in isolated symptomatic lesions and cannot affect the multitude of atherosclerotic lesions throughout the body.

Theories relating to the etiology of atherosclerosis are many and vary from genetic and ecologic factors to levels of lipids in the bloodstream to injury of the arterial wall.

A safe and effective treatment for atherosclerosis has been the goal of investigators for a substantial period of time. Such a technique to be successful in the destruction of the arterial lesions must be selective in effect upon the atherosclerotic lesions and produce no irreversible damage to the normal blood vessel. In sum, the treatment of atherosclerosis must selectively differentiate the atherosclerotic portions of the vessel wall from the normal portions of the vessel wall and must selectively destroy the atherosclerotic lesions without affecting the normal vessel.

It has been known that there are certain physical differences that exist between atherosclerotic lesions and a normal blood vessel. One primary physical difference that exists is that atherosclerotic plaques and certain extravascular related lesions (xanthomas, corneal arcus) arise because altered endothelial permeability allows certain macromolecular plasma proteins (which are normally confined to the circulation i.e. lipids) to permeate endothelium and interact with charged components of the connective tissue gel of the vessel wall. The early lesions of atherosclerosis, the fatty streaks and fibrous plaques show evidence of altered permeability in allowing the uptake of protein-bound dyes (trypan blue), colloidial carbon or labeled cholesterol. These substances are taken up by the atherosclerotic lesion but not by the normal blood vessel wall. The normal intima presents a barrier, metabolic or structural, to the influx of serum cholesterol. During atherogenesis this barrier breaks down permitting the entry of blood consistuents. This increased permeability has been theorized to be secondary to the release of histamine, kinins, an immunologic reaction or to previous injury or stress. With this increase in permeability there is an uptake of particles normally excluded form the vessel wall.

In addition it has been shown that to a large extent atherosclerotic lesions are monoclonal in nature and result from the overgrowth and excessive proliferation of a single cell line much like a tumor. Proliferation of endothelial and medial smooth muscle cells occurs secondary to trauma or to hyper-cholesterolemia. These proliferating cells take in foreign particles to a high degree.

It is known, therefore, that the atherosclerotic lesion will take in large amounts of particles secondary to increased permeability. Furthermore, the proliferating cells of the atherosclerotic lesion (endothelial and medial smooth muscle cells), phagocytize these particles. The particles are, therefore, intracellular in these cells of the atherosclerotic lesion as well as being located between the endothelial cell and the internal elastic membrane of the vessel.

The atherosclerotic lesion, itself, contains a large number of particles which can act as an electric or magnetic dipole. The plaque besides containing a large amount of hemoglobin and hemosiderin also contains a large amount of iron.

BRIEF DESCRIPTION OF THE INVENTION

This instant invention relates to eliminating the atherosclerotic lesions selectively by intracellularly and extracellularly generating a temperature and by changing biophysical characteristics and/or structural properties resolving the atherosclerotic lesion without affecting the normal vessel.

DETAILED DESCRIPTION OF THE INVENTION

The instant invention achieves a precise increment of heat rise within the atherosclerotic lesion and within the cytoplasm of the cells. The thermal barrier that characteristically exists as the outer membrane or cell wall of the cell is now utilized as a means of retaining the heat produced within the cell, rather than, as in the past preventing any heat build-up within the cell. By raising the temperature of the intracellular particles as well as the particles between the endothelial cells and the internal elastic membrane in the atherosclerotic lesion the atherosclerotic lesion is resolved without affecting the normal vessel.

In accordance with the instant invention, there are found to be a number of approaches that can successfully achieve the end result of an intracellular and extracellular heat rise with resolution of the atherosclerotic lesion.

In its simplest and broadest aspect the instant invention contemplates the use of the ferromagnetic, paramagnetic or diamagnetic particles already located in the atherosclerotic plaque with the entire body being subjected to an alternating electromagnetic field.

The inductive heating of the minute particles is achieved by using an electronic oscillator operating in the high frequency range which heats the particles by subjecting them to an intense high-frequency field within a large but otherwise conventional helical coil, field energy being converted to heat through hysteresis losses and the resistive dissipation of eddy currents. The helical inductive coil is of sufficient internal diameter to permit the subject to pass within and of such length to encompass the length of the subject. Generally, the internal diameter should be at least 2 feet, but preferably would be greater than 3-6 feet in diameter. No maximum diameter is known to exist except that required form practical and economical considerations. Diameters of inductive coils of greater than 6 feet have a preferential effect in the overall process by providing a more uniform flux gradient to the subject.

The frequency of the electromagnetic alternating high frequency field will range from 1 hertz to 100 megahertz and the power input f the oscillator-generator will range from 0.5 kilowatts per kg. of subjects's body weight 0.75 kilowatts of power per 1.0 kilograms of body weight has been found to particularly useful. In this power and frequency range, the coil is selected to produce from 200–1000 oersteds, preferably 550–650 oersteds, but may function from 100–70,000 oersteds, as well as other variations.

The time necessary to inductively heat the minute particles held within the cells and the atherosclerotic lesions to be treated depends substantially upon the frequency and the power producing the alternating electromagnetic field and ultimately the strength of the field produced. In general, it has been found that subjecting the subject to 5 to 12 minutes or preferably 8 to 10 minutes of the alternating electromagnetic field would be adequate to bring about the necessary temperature rise of approximately 9.0° Centigrade and that the variables with respect to the type and concentration of the particles in the vehicle and the electromagnetic treatment are not critical provided that the necessary temperature is achieved to resolve the atherosclerotic lesion. In further embodiment, since the instant invention provides the possibilities for specific particle distribution and a sensing of the responsiveness to the various treatment fields, high temperature treatment modalities are also possible. The 9.0° Centigrade temperature rise as discussed supra is, of course, predicated on the situation in which particle distribution, magnetic state, and orientation were equal in all cells and in the atherosclerotic lesions, under the treatment conditions. However, employing the methods of this instant invention thereby affecting specific particle distribution, orientation, differential magnetic susceptibility, timing and other parameters described herein, within cells and atherosclerotic lesions in the target area, increases in the intracelllular temperature up to 100° Centigrade are possible without substantially damaging surrounding tissues and cells and without injuring the normal blood vessel.

Biological alterations are induces by the energy input to the particle and thereupon to the interior of the cells and the atherosclerotic lesions. Thus, the same energy input may be accomplished by application over a long period of time with a consistent small temperature rise for 10–20 minutes or when the same total amount of energy is applied over a short period of time a higher temperature results (100° C. for a few seconds). Obviously, timing and energy parameters may be adjusted to provide a spectrum of intracellular temperature which may be utilized in this instant invention depending upon the treatment appropriate in specific cases.

Where necessary, a biopsy of the atherosclerotic lesion can be used to determine the ideal frequency to be used in the treatment method through in-vitro studies. However, in general this would not be necessary.

In addition, a local probe may be utilized by threading a catheter in the blood vessel either percutaneously, at the time of surgery or around the blood vessel. This probe may also be magnetically guided to the area of interest. The probe then creates an alternating electromagnetic field to treat the atherosclerotic lesion locally. The probe may also create a steady magnetic field to help induce electric and magnetic dipoles in the atherosclerotic plaque to be treated.

As further embodiment of this instant invention, a stationary magnetic field in the range of 100 oersteds to 70,000 oersteds can be used before, during or after treatment to help induce electric and magnetic dipoles and thereby enhance the treatment modality. This provides a means of further enhancement of the use of electric and magnetic dipoles present or capable of being induced within the atherosclerotic lesion and the cells located therein. described in U.S. Pat. No. 4,359,453.

In addition, an atherosclerotic seeking agent exclusive of said particles, electric and magnetic dipoles, may be used in a concentration sufficient to combine with and selectively direct the particles, electric and magnetic dipoles, to the atherosclerotic lesions.

The particles are selected from the group comprising ferromagnetic, paramagnetic and diamagnetic elements, inorganic compounds, organic compounds, and combinations thereof such as particles or dipoles based on compounds selected from the group comprising cobalt, zinc, iron, chromium, nickel, platinum, rare earth metals such as dysprosium, erbium, europium, gadolinium, holmium, samarium, terbium, thulium, ytterbium, yttrium and compounds thereof such as dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide ($Y_3Fe_5O_{12}$), yttrium aluminium oxide ($Y_3Al_5O_{12}$), dysprosium-nickel, dysprosium cobalt, gadolinium-iron, ytterbium-iron, cobalt-samarium, gadolinium-ytterbium, dysprosium-gallium, and actinide series elements and compounds thereof and combinations thereof as well as organic compounds selected from the group comprising:

(a) dextran metal complexes wherein said metal is selected from the group consisting of cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium, and iron such as $Fe_2O_3$ particles, $Fe_3O_4$ particles and FeOOH particles and $Fe_2O_3$-dextran complexes, $Fe_3O_4$-dextran complexes, and FeOOH-dextran complexes;

(b) iron transporting and chelating compounds comprising ferric ammonium citrate, enterochelin, transferrin, metallothionein, hydroxamates, phenolates, ferrichromes, desferriferrichromes, ferritin, ferric mycobactins and iron sulfur proteins such as ferredoxin and rubredoxin;

(c) porphyrins comprising etioporphyrins, mesoporphyrins, uroporphyrins, coproporphyrins, protoporphyrins, dicarboxylic acid containing porphyrins, substituted porphyrins such as tetraphenylporphyrin sulfonate and protoporphyrin containing molecules such as hematoporphyrins, chlorophylls, and cytochromes; and combinations thereof.

Additionally, the natural occurring metal moiety of said porphyrin may be optionally substituted with a metal selected from the group comprising cobalt, zinc, chromium, gallium, iron, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium; and combinations thereof. The above iron transporting, iron chelating and porphyrin compounds may be chemically complexed with dextran which in turn may be chemically complexed with an antibody.

The particles or dipoles are also made from metal-organic compound complexes are selected from the group comprising Fe(III) Tetraphenylporphyrin sulfonate (TPPS$_4$) Acetate, Fe(III) TPPS$_4$ Acetate 4Na Salt (H$_2$O), Fe(III) Mesoporphyrin IX Chloride, Fe(III) TPPS$_4$ Chloride, Co TPPS$_4$, Co(III) MesoTPPS$_4$ Tetra Na Salt (Acetate), Fe Phthalocyanine Tetrasulfonate Tetra sodium salt, Tetra Sodium-meso-Tetra (4-sulfonate-phenyl) Porphine (12 hydrate), Fe(III) Tetra (N-Methyl 4-Puridyl) Porphyrin Pentachloride, Fe Phthalocyanine, Hemin, Fe-Hematoporphyrin D. (HPD), Fe-Acetoxyethyl vinyl Deuteroporphyrin, Fe-Protoporphyrin IX, Fe-Deuteroporphyrin 2,4 bis acetal, Mn-TPPS$_4$, Co-N+MTPyP, Mn-N+MTPyp, Co-Mesoporphyrin X, Protohemin, Deuterohemin, Meso-tetra (4-N methyl pyridyl) hemin tetraiodide, Meso-tetra (4-carboxy phenyl) hemin, Ni-TPPS, NI-HPD, Mn-Mesoporphyrin IX, Co-Protoporphyrin IX, Mn-Protoporphyrin IX, Sn-Protoporphyrin IX, Co-HPD, Mn-HPD, Gd-TPPS, Gd-HPD, Hematoporphyrin Mono-acetate-Fe, Ferretin-Fe, Ferredoxin-Fe(4), Transferrin-Fe, Hematoporphyrin Diacetate-Gd, GdFe$_2$-TPPS$_4$, GdFe$_2$-HPD, FeTPPS$_4$(OH$_2$)$_2$ ClO$_4$—, FeTPP(OH$_2$)$_2$ ClO$_4$—, Fe-nitrolacetate, Fetertrasulfinated phalocyanine, Bisimidozole (FeTPPS)ClO$_4$— Rubrium-ferricytochrome/c; and combinations thereof optionally chemically complexed with dextran which in turn may be chemically complexed with an antibody.

What is claimed is:

1. A process for the use of any ferromagnetic, paramagnetic, or diamagnetic particles, electric or magnetic dipoles already in an atherosclerotic lesion by the application of external electromagnetic energy capable of generating heat to alter the biophysical and/or structural properties intracellularly and extracellularly of said atherosclerotic lesions to induce the resolution of said lesion comprising:

subjecting a host having an atherosclerotic lesion to an alternating electromagnetic field to inductively heat and alter the biophysical and/or structural properties of said particles, electric or magnetic dipoles already in said atherosclerotic lesions, and thereby alter the atherosclerotic lesions, continuing the inductive heating of said particles, electric or magnetic dipoles already in said atherosclerotic lesions to resolve said atherosclerotic lesions.

2. A process wherein minute ferromagnetic, paramagnetic or diamagnetic particles, electric or magnetic dipoles are intravenously or intraarterially injected into a host having atherosclerotic lesions, said particles being capable of being inductively heated and of a size less than or not more than about 1 micron, so that said particles, electric or magnetic dipoles are selectively absorbed intracellularly and extracellularly into an atherosclerotic lesion, in said host having said lesions, subjecting said host to an alternating electromagnetic field to inductively heat said particles, electric or magnetic dipoles in said atherosclerotic lesions and alter the biophysical and/or structural properties of said atherosclerotic lesion, continuing said inductive heating of said particles in said atherosclerotic lesions and said electric and magnetic dipoles to resolve said atherosclerotic lesions; said particles and dipoles being selected from the group comprising cobalt, zinc, chromium, nickel, platinum, rare earth metals such as dysprosium, erbium, europium, gadolinium, holmium, samarium, terbium, thulium, ytterbium, yttrium and compounds thereof such as dysprosium sulfate, erbium sulfate, europium oxide, europium sulfate, gadolinium oxide, gadolinium sulfate, holmium oxide, samarium sulfate, terbium sulfate, thulium oxide, ytterbium sulfide, yttrium oxide, yttrium sulfate, yttrium ferrioxide (Y$_3$Fe$_5$OH$_{12}$), yttrium aluminum oxide (Y$_3$Al$_5$O$_{12}$), dysprosium-nickel, dysprosium cobalt, gadolinium-iron, ytterbium-iron, cobalt-samarium, gadolinium-yttrbium, dysprosium-gallium, and actinide series elements and compounds thereof, dextran metal complexes, iron transporting and chelating compounds and porphyrins; and mixtures thereof.

3. The process of claim 1 including an atherosclerotic seeking agent exclusive of said particles, electric and magnetic dipoles, in a concentration sufficient to combine with and selectively direct said particles, electric and magnetic dipoles, to said atherosclerotic lesions.

4. The process of claim 2 where said particles and dipoles are organic compounds selected from the group comprising:

(a) dextran metal complexes wherein said metal is selected from the group consisting of cobalt, zinc, chromium, iron, gallium, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium, and iron such as Fe$_2$O$_3$ particles, Fe$_3$O$_4$ particles and FeOOH particles and Fe$_2$O$_3$-dextran complexes, Fe$_3$O$_4$-dextran complexes, and FEOOH-dextran complexes;

(b) iron transporting and chelating compounds comprising ferric ammonium citrate, enterochelin, transferrin, metallothionein, hydroxamates, phenolates, ferrichromes, desferriferrichromes, ferrithin, ferric mycobactins and iron sulfur proteins such as ferredoxin and rubredoxin;

(c) porphyrins comprising etioporphyrins, mesoporphyrins, uroporphyrins, coproporphyrins, protoporphyrins, dicarboxylic acid containing porphyrins, substituted porphyrins such as tetraphenylporphyrin sulfonate and protoporphyrin containing molecules such as hematoporphyrins, chlorophylls, and cytochromes; and combinations thereof.

5. The process according to claim 4 wherein said porphyrin contains a natural occurring metal moiety optionally being substituted with a metal selected from the group comprising cobalt, zinc, chromium, gallium, iron, manganese, nickel, platinum, dysprosium, erbium, europium, gadolinium, holmium, samarium, terbium, thulium, ytterbium, yttrium, dysprosium-nickel, dysprosium-cobalt, gadolinium-iron, ytterbium-iron, cobalt-samarium, gadolinium-yttrium, and dysprosium-gallium; and combinations thereof.

6. The process according to claim 4 or 5 wherein said iron transporting, iron chelating and porphyrin compounds are chemically complexed with dextran.

7. The composition according to claim 6 wherein said particles are chemically complexed with an antibody.

8. The process according to claim 4 wherein said compounds are selected from the group comprising Fe(III) Tetraphenylporphyrin sulfonate (TPPS$_4$) Acetate, Fe(III) TPPS$_4$ Acetate 4Na Salt (H$_2$O), Fe(III) Mesoporphyrin IX Chloride, Fe(III) TPPS$_4$ Chloride, Co TPPS$_4$, Co(III) MesoTPPS$_4$ Tetra Na Salt (Acetate), Fe Phthalocyanine Tetrasulfonate Tetra sodium salt, Tetra Sodium-meso-Tetra (4-sulfonate-phenyl) Porphine (12 hydrate), Fe(III) Tetra (N-Methyl 4-Puridyl) Prophyrin Pentachloride, Fe Phthalocyanine, Hemin, Fe-Hematoporphyrin D. (HPD), Fe-Acetoxyethyl vinyl Deuteroporphyrin, Fe-Protoporphyrin IX, Fe-Deuteroporphyrin 2,4 bis acetal, Mn-TPPS$_4$, Co-+MTPYP, Mn-N+MTPyp, Co-Mesoporphyrin X, Protohemin, Deuterochemin, Meso-tetra (4-N methyl pyridyl) hemin tetraiodide, Meso-tetra (4-carboxy phenyl) hemin, Ni-TPPS, Ni-HPD, Mn-Mesoporphyrin IX, Co-Protoporphyrin IX, Mn-Protoporphyrin IX, Sn-Protoporphyrin IX, Co-HPD, Mn-HPD, Gd-TPPS, Gd-HPD, Hematoporphyrin Mono-acetate-Fe, Ferretin-Fe, Ferredoxin-Fe(4), Transferrin-Fe, Hematoporphyrin Diacetate-Gd, GdFe$_2$-TPPS$_4$GdFe-HPD, FeTPPS$_4$(OH$_2$)$_2$ ClO$_4$—, FeTPP(OH$_2$)$_2$ ClO$_4$—, Fe-nitrolacetate, Fetetrasulfinated phalocyanine, Bisimidozole (FeTPPS)ClO$_4$—, Rubrium-ferricytochrome/c, and combinations thereof.

9. The process according to claim 8 wherein said compounds are chemically complexed with dextran.

10. The process according to claim 9 wherein said compounds are chemically complexed with an antibody.

11. The process of claim 3 wherein said atherosclerotic seeking agent is an atherosclerotic specific antibody.

12. The process of claim 1 or 2 wherein a biopsy of the atherosclerotic plaque is obtained and exposed to said alternating electro magnetic field at various frequencies to determine the ideal frequency with which to treat the atherosclerotic lesion and exposing said host to said field at said ideal frequency.

13. The process of claim 1 or 2 wherein as part of said process, a stationary magnetic field is used before, during or after treatment to help induce electric and magnetic dipoles in the atheorosclerotic plaque to be treated.

14. The process of claim 1 or 2 wherein, as part of said process an oscillating or pulsed electromagnetic field is used before, during or after treatment to help induce electric and magnetic dipoles in the atherosclerotic plaque to be treated.

15. The process of claim 1 or 2 wherein a local probe is utilized in the blood vessel or around the blood vessel to create an alternating electromagnetic field to treat the atherosclerotic lesion.

16. The process of claim 1 or 2 wherein a local probe is utilized in the blood vessel or around the blood vessel to create a stationary magnetic field to help induce electric and magnetic dipoles in the atherosclerotic plaque to be treated.

* * * * *